(12) United States Patent
Yoshinaga et al.

(10) Patent No.: US 7,572,579 B2
(45) Date of Patent: Aug. 11, 2009

(54) SCREENING METHOD FOR A RIBONUCLEASE H INHIBITOR OF A REVERSE TRANSCRIPTASE

(75) Inventors: Tomokaz Yoshinaga, Settsu (JP); Takao Shishido, Settsu (JP)

(73) Assignee: Shionogi & Co., Ltd., Osaka-shi (JP)

( * ) Notice: Subject to any disclaimer, the term of this patent is extended or adjusted under 35 U.S.C. 154(b) by 278 days.

(21) Appl. No.: 10/590,115

(22) PCT Filed: Feb. 25, 2005

(86) PCT No.: PCT/JP2005/003100

§ 371 (c)(1),
(2), (4) Date: Oct. 27, 2006

(87) PCT Pub. No.: WO2005/083112

PCT Pub. Date: Sep. 9, 2005

(65) Prior Publication Data

US 2007/0178444 A1    Aug. 2, 2007

(30) Foreign Application Priority Data

Feb. 27, 2004 (JP) .............................. 2004-052627

(51) Int. Cl.
*C12Q 1/68* (2006.01)
(52) U.S. Cl. ......................................................... 435/6
(58) Field of Classification Search ........................ None
See application file for complete search history.

(56) References Cited

FOREIGN PATENT DOCUMENTS

WO    WO-03/103610 A2    12/2003

OTHER PUBLICATIONS

Palaniappan et al., "Mutations within the Primer Grip Region of HIV-I Reverse Transcriptase Result in Loss of Rnase H Function", vol. 272, pp. 11157-11164 (1997).

Arts et al., "Interaction of Retroviral Reverse Transcriptase with Template-Primer Duplexes during Replication" vol. 58, pp. 339-393 (1998).
Shaw-Reid et al., "Inhibition of HIV-1 Ribonuclease H by a Novel Diketo Acid, 4-[5-(Benzoylamino)thein-2-yl]2,4-dioxobutanoic Acid", The Journal of Biological Chemistry, vol. 278, pp. 67-109 (2000).
Rychetsky et al., "Development of a Nonradioactive Ribonuclease H Assay",Analytical Biochemistry 239, 113-115 (1996).
Palaniappan et al., "Nevirapine Alters the Cleavage Specificity of Ribonuclease H of Human Immunodeficiency Virus 1 Reverse Transcriptase" Journal Biological Chemistry, vol. 270, pp. 4861-4869 (1995).
Snyder et al., "Comparison of Second- Strand Transfer Requirements and Rnase H Cleavages Catalyzed by Human Immunodeficiency Virus Type 1 Reverse Transcriptase (RT) and E478Q RT", Journal of Virology, pp. 9668-9679, Oct. 2000, vol. 74, No. 20.
Parniak et al., "A fluorescence-based high-throughoutput screening assay for Inhibitors of human immunodeficiency virus- reverse transcriptase-assocaited ribonuclease H activity", Analytical Biochemistry., vol. 322, No. 1, pp. 33-39 (2003).
McLellan et al., "Nonradioactive Detection of Retroviral-Associated Rnase H Activity in a Microplate-Based, High-Throughput Format" BioTechniques 33:424-429 (Aug. 2002).
Shao et al., "Colorimetric asays for evaluation of the mode of action of human immunodeficiency virus type 1 non-nucleoside reverse transcriptase inhibitors", Antiviral Chemistry & Chemotherapy, vol. 9, No. 2, pp. 167-176 (1998).
Fan et al., Simultaneous mutations at Tyr-181 and Tyr-188 in HIV-1 reverse transcriptase prevents inhibition of RNA-dependent DNA polymerase activity by the bisheterorarylpiperazine (BHAP) U-90152s, Federation of European Biological Societies, vol. 370, Nos. 1 & 2, pp. 59-62 (1995).

*Primary Examiner*—Kenneth R. Horlick
*Assistant Examiner*—David C Thomas
(74) *Attorney, Agent, or Firm*—Birch, Stewart, Kolasch & Birch LLP (57) ABSTRACT

A screening method for a compound which inhibits a ribonuclease H activity of a reverse transcriptase which includes incubating a substrate with an appropriate primer hybridized to an appropriate template, a metal ion and a reverse transcriptase to form a complex, adding a test substance, and after these steps adding dNTPs to initiate DNA synthesis, measuring the amount of nucleic acid cleaved from the template, and comparing the measured value with a measured value in the absence of a test substance.

12 Claims, 2 Drawing Sheets

$$IC_{50 \text{ value}} = B-(Y-50)(B-A) / (Y-X)$$
$$= 33.3-(61.1-50)(33.3-11.1) / (61.1-35.3)$$
$$= 24$$

SCREENING METHOD FOR A RIBONUCLEASE H INHIBITOR OF A REVERSE TRANSCRIPTASE

FIELD OF THE INVENTION

The present invention relates to a screening method for a compound which inhibits an activity of a reverse transcriptase. In more detail, it relates to a screening method for a ribonuclease H (RNase H) inhibitor of a reverse transcriptase.

PRIOR ART

Acquired immunodeficiency syndrome (AIDS) is a main cause of death for human beings even now. This pathogen, a retrovirus, multiplies in a host cell with three virus-specific enzymes, a reverse transcriptase, an integrase and a protease. Therefore, so far, a new compound that inhibits the activity of a virus-specific enzyme is required to develop a preventive agent and a therapeutic agent of a disease caused by a retrovirus.

It's known that a reverse transcriptase, which is one of retrovirus-specific enzymes, binds to double-stranded nucleic acid at a nucleic acid binding site and then synthesizes DNA from a RNA template. It has two enzymatic activities, which are the polymerase activity and the RNase H activity. Though biochemical and structural measurements show that a distance between an active center of a polymerase and an active center of an RNase H is about 18 nucleotides along the template, it is estimated that the distance varies about 14-20 nucleotides depending on a sequence of the nucleic acid (Non-patent document 1). Divalent metal ions are necessary to bind each active site for each enzymatic activity, and the RNA template is reverse transcribed at the polymerase active site and the RNA strand of RNA: DNA hetero duplex is hydrolyzed at the RNase H active site.

The polymerase activity of a reverse transcriptase is an enzymatic activity for DNA synthesis and needs a template and a primer for initiation of the DNA synthesis. Both RNA and DNA can be utilized as the template and the primer. RNase H has two modes of cleavage, one is (i) the polymerization-dependent RNase H activity which cleaves RNA template along with DNA synthesis, the other is (ii) the polymerization-independent RNase H activity which cleaves RNA when a reverse transcriptase binds to double-stranded nucleic acid and RNA: DNA hetero duplex is at the RNase H active site without DNA synthesis (Non-patent document 2).

All current approved anti-retrovirus agents as a reverse transcriptase inhibitor are compounds which bind at a polymerase active site or at a nonnucleoside binding site to inhibit a polymerase activity (Non-patent document 3). Therefore, RNase H inhibitor can be a new mechanism agent and is expected to have an effect on all resistant viruses against polymerase, integrase or protease inhibitors. Until now, although 4-[5-(benzoylamino)thien-2-yl]-2,4-dioxobutanoic acid (Non-patent document 4) has been reported as a compound which specifically inhibits the RNase H activity without inhibiting the polymerase activity of HIV reverse transcriptase, this compound can not inhibit virus proliferation in cell-based assay. On the other hand, it has been reported that mappicine analogs can inhibit the RNase H activity and inhibit virus proliferation in cell-based assay (Patent document 1).

To screen a reverse transcriptase inhibitor which inhibits the RNase H activity, it needs to measure the RNase H activity. In an RNase H activity assay which has been reported, a RNA template and a DNA primer are used generally to make RNA: DNA hetero duplex by hybridizing both strands and this is used as a substrate for RNase H under the presence of a metal ion (Non-patent document 5). This method has adapted to screening for an RNaseH inhibitor, in which a reverse transcriptase is added finally to a reaction mixture containing a substrate, a metal ion and a test substance to initiate RNase H reaction (Patent document 1). However, under this condition, when a reverse transcriptase-substrate complex (a complex of a reverse transcriptase and a substrate that a primer is hybridized to a template) is formed once, the template is cleaved immediately by RNase H activity of a reverse transcriptase. After the template is cleaved, the enzyme leaves from the substrate, turns over and binds to the other substrate. Therefore, there are several possibilities as to a site of action of a test substance obtained as a candidate for a reverse transcriptase inhibitor and a further experiment is necessary to distinguish these sites of action. Furthermore, because RNase H reaction is very rapid, the test substance binds to a reverse transcriptase-substrate complex and inhibits RNase H activity, there is not enough time for the test substance to bind to a reverse transcriptase-substrate complex. Furthermore, because a reverse transcriptase-substrate complex formation takes more time than RNase H reaction, there is a high possibility that not an RNase H inhibitor but a reverse transcriptase-substrate complex formation inhibitor is obtained and this method is very inefficient as a screening for an RNase H inhibitor.

To compensate for these defaults, an assay that after pre-incubating a reverse transcriptase, a substrate and a test substance under the absence of a metal ion which is essential for the expression of RNase H activity, a metal ion is added to initiate an enzyme reaction is used (Non-patent documents 4 and 6). However, a reverse transcriptase-substrate complex is formed in the absence of a metal ion in this assay, this does not reflect the complex in host cells. Therefore, in this assay, pre-incubation of a reverse transcriptase-substrate complex and a test substance is performed in the situation that does not reflect in host cells. Consequently, there is possibility that a compound obtained from this assay system does not work in a host cell.

As to the RNase H activity of a reverse transcriptase, there remain many unclear points and the researches to clarify the reaction mechanism are performed by reproducing in vitro a reverse transcription reaction in a host cell. There is a document that a reverse transcriptional reaction in a host cell is reproduced in vitro by using a RNA-DNA chimeric template and a DNA primer (Non-patent document 7). However, in this document, the sequence of the template and the primer is derived from HIV genomic RNA and a concept of preincubation is not disclosed. Therefore, this document does not indicate a screening for a medicine or the like.

Patent document 1: WO 03/103610

Non-patent document 1: C. Palaniappan et al., The Journal of Biological Chemistry (J. Biol. Chem.), Vol. 272, pp. 11157-11164 (1997)

Non-patent document 2: Arts, E. J., et al., Progress in Nucleic Acid Research and Molecular Biology (Pro Nucleic Acid Res Mol Biol.), Vol. 58, pp. 339-393 (1998)

Non-patent document 3: Parniak, M. A., et al., Advanced Pharmacology (Adv. Pharmacol.), Vol. 49, pp. 67-109 (2000)

Non-patent document 4: C. A. Shaw-Reid, et al., The Journal of Biological Chemistry (J. Biol. Chem.), Vol. 278, pp. 2777-2780 (2003)

Non-patent document 5: P. Rychetsky, et al., Analytical Biochemistry (Anal. Biochem.), Vol. 239, pp. 113-115 (1996)

Non-patent document 6: C. Palaniappan, et al., The Journal of Biological Chemistry (J. Biol. Chem.), Vol. 270, pp. 4861-4869 (1995)

Non-patent document 7: M. J. Roth, et al., Journal of Virology (J. Virol.), Vol. 74, p. 9668-9679 (2000)

DISCLOSURE OF INVENTION

Problems to be Solved by the Invention

The present invention provides a screening method for an RNase H inhibitor which overcame the defaults of the above conventional methods. To be more precise, it provides a new screening method for an RNase H inhibitor, which improved the detectability of the inhibitor which can act on for a functional reverse transcriptase-substrate complex formed in a host cell. Additionally, the present invention provides how to screen easily and rapidly an RNase H inhibitor by the screening method.

Means to Solve the Problems

The present inventors have intensively studied to enhance detectability of a screening method for an RNase H inhibitor. They considered the necessity to preincubate a test substance and a reverse transcriptase-substrate complex bonded a metal ion which formed in a host cell by nature. With an appropriate template and an appropriate primer, a reverse transcriptase-substrate complex was formed under the presence of a metal ion without both DNA synthesis reaction (polymerase reaction) and RNase H reaction, and a test substance could be preincubated with the complex.

A substrate in the present invention is described as below.

The present invention needs to use a substrate which has RNA: RNA or DNA: DNA homo duplex at a corresponding part to an RNase H active site of the reverse transcriptase when a reverse transcriptase-substrate complex is formed. For example, a substrate that all part of the double strand is homo duplex can be used. By using the substrate, the initiation of RNase H reaction is prevented. Therefore, a test substance and a reverse transcriptase-substrate complex can be preincubated under the presence of a metal ion.

By adding dNTPs, the polymerase reaction is proceeded and the reverse transcriptase moved to the 5'-end of the template. Therefore, in the present invention, it needs to use a template which forms hetero duplex composed of both RNA part of template and newly synthesized DNA by polymerase reaction at a corresponding part to an RNase H active site when a reverse transcriptase moved at the 5'-end of the template.

By using the template, dNTPs are added after the preincubation with a test substance to initiate a polymerase reaction. A reverse transcriptase moves and RNase H active site is moved to the RNA: DNA hetero duplex part. Then, the template is cleaved and the amount of cleaved nucleic acid is measured to estimate the inhibitory activity against an RNase H of the substance.

With the above substrate, a compound which specifically inhibits the RNase H activity without inhibiting the polymerase activity can be screened.

Additionally, a compound which inhibits the RNase H activity and the polymerase activity at a time by binding an RNase H domain is also a reverse transcriptase inhibitor through a new action mechanism and is described as an RNase H inhibitor in this description. However, because the RNase H inhibitory activity and the polymerase inhibitory activity express equivalence, the measurement result is almost same with the result of a reverse transcriptase inhibitor by the well-known mechanism of action (a compound which inhibits the polymerase activity by binding to a polymerase active site or to a nonnucleoside binding site). As to an RNase H inhibitor of this mechanism, the experiment with an enzyme which has a mutation at an RNase H active site or the like is performed to identify a mechanism of action. In the other word, as to a test substance which inhibits the RNase H activity and the polymerase activity at a time, by using a well-known reverse transcriptase with a mutation near a polymerase active site, for example, a Y188L mutant enzyme or the like, or a well-known reverse transcriptase with a mutation near an RNase H active site, for example, a Y501W mutant enzyme or the like, it is possible to clarify whether the test substance binds to a polymerase active site or an RNase H active site and regulates the function or not. A test substance, which shows the inhibitory activity when a wild type reverse transcriptase is used but does not show the inhibitory activity when the above mutant enzyme is used, regulates a function of a reverse transcriptase by binding to a site which is the mutant position of the mutant enzyme.

A metal ion is known as an essential factor for activities of a reverse transcriptase and to bind at both an RNase H active site and a polymerase active site. By using a well-known reverse transcriptase with a mutation at a polymerase active site, for example, a D185N mutant enzyme or the like, or a well-known reverse transcriptase with a mutation at an RNase H active site, for example, a D443N mutant enzyme or the like, it is possible to detect whether the test substance binds directly through a metal ion to a polymerase active site or an RNase H active site and regulates the function or not. A test substance, which shows inhibitory activity when a wild type reverse transcriptase is used but does not show the inhibitory activity when the above mutant enzyme is used, regulates the function of the reverse transcriptase by binding directly through a metal ion to the site which is the mutant position of the mutant enzyme.

The present invention is (1) A screening method for an RNase H inhibitor of a reverse transcriptase, comprising;

(a) a process to incubate a substrate which a primer hybridized to a template, a metal ion and a reverse transcriptase to form a complex, (b) a process to add a test substance after the process (a) and incubate, and (c) a process to add dNTPs after process (b) to initiate DNA synthesis, provided that, the template is 5'-NRWXZ-3' and the primer is 3'-Y-5' (Y hybridizes to X of a template), the template is 5'-NRWX-3' and the primer is 3'-YZ-5' (Y hybridizes to X of a template), or the substrate is 5'-NRWXZY-3' (Y hybridizes to X), wherein, N is 13-19 mer DNA, RNA or a chimeric nucleic acid, R is RNA, W is DNA or a chimeric nucleic acid, X is 15 mer or more DNA, RNA or a chimeric nucleic acid, Y is a same length DNA, RNA or a chimeric nucleic acid with X to which Y hybridizes.

In case that X to which Y hybridizes is DNA, Y is DNA. In case that X to which Y hybridizes is RNA, Y is RNA. In case that X to which Y hybridizes is a chimeric nucleic acid, Y is a chimeric nucleic acid (In the chimeric nucleic acid, in case that X to which Y hybridizes is DNA, Y is DNA. In case that X to which Y hybridizes is RNA, Y is RNA).

Z is DNA, RNA or a chimeric nucleic acid (provided that, W and Z can be absent), (2) the screening method of (1), wherein N is RNA, W is absent, X is RNA, and Y is RNA, (3) the screening method of (1), wherein N is RNA, W is absent, X is DNA, and Y is DNA, (4) the screening method of any one of (1)-(3), wherein X is 18 mer or more DNA, RNA or a chimeric nucleic acid, (5) the screening method of any one of (1)-(3), wherein the metal ion is $Mg^{2+}$ or $Mn^{2+}$, (6) the screening method of (1), wherein a formation inhibitor to a complex of a reverse transcriptase, a substrate and a metal ion is added with dNTPs in process (c), (7) the screening method of (6), wherein the formation inhibitor is heparin, (8) the screening method of (1), comprising;

after the process (c), (d) a process to measure the amount of nucleic acid cleaved from the template, and (e) a process to compare the measured value with a measured value under the absence of a test substance, (9) the screening method of (8), wherein the template is a template whose 5'-end or 3'-end is labeled, (10) the screening method of (1), wherein the reverse transcriptase is a reverse transcriptase of a virus, (11) the screening method of (10), wherein the virus is HIV, (12) the screening method of (10), wherein the reverse transcriptase is a Y188L mutant enzyme.

Effect of the Invention

With a screening method of the present invention, an RNase H inhibitor of a reverse transcriptase can be screened easily and rapidly. Additionally, with this screening method, a candidate compound of an anti-virus drug which effects on a resistant virus of a polymerase inhibitor, an integrase inhibitor and a protease inhibitor can be screened.

BEST MODE FOR CARRYING OUT THE INVENTION

"A screening method for a H type ribonuclease inhibitor of a reverse transcriptase" which is a screening method of the present invention is characterized by preincubating a test substance with a complex of a substrate that a primer hybridized to a template and a reverse transcriptase under the presence of metal ion before the initiation of enzyme reactions to perform a easier and rapider screening than conventional methods.

"A reverse transcriptase" means an enzyme having both the polymerase activity that is to bind to double-stranded nucleic acid and to synthesize complementary DNA with RNA and DNA as a template and the RNase H activity that is to cleave only RNA part of RNA: DNA hetero duplex. A reverse transcriptase needs an RNA or DNA primer to initiate the reaction as well as a DNA polymerase. A different point from a DNA polymerase is that a reverse transcriptase can use RNA as a template.

As "a reverse transcriptase", a reverse transcriptase of a virus is especially preferable. A virus having a reverse transcriptase is a virus belonging to Retroviridae. Retroviridae includes Lentivirinae, Oncovirinae, spumavirinae or the like. A virus in Lentivirinae is, for example, Human immunodeficiency virus (HIV). A virus in Oncovirinae is, for example, Sarcoma virus, Human T-lymphotropic virus (HTLV), Mammary tumor virus or the like. Especially, HIV is preferable.

"An RNase H inhibitor" means a compound that specifically inhibits the RNase H activity without inhibiting the polymerase activity or a compound that inhibits by a new mechanism which is to inhibit the RNase H activity and the polymerase activity at a time by binding to an RNase H domain.

A "nucleic acid" means a high-molecular substance whose unit is a nucleotide that a phosphate group is linked by an ester bond to a sugar molecule of a nucleoside that a base is linked to a sugar by a covalent bond.

"DNA" is a nucleic acid constructed from nucleotides whose sugar parts are deoxyribose and comprising bases selected from adenine, guanine, cytosine and thymine. In this description, 1 mer or more nucleic acid, which is constructed from the above nucleotide, is called as DNA.

"RNA" is a nucleic acid constructed from nucleotides whose sugar parts are ribose and comprising bases selected from adenine, guanine, cytosine and uracil. In this description, 1 mer or more nucleic acid, which is constructed from the above nucleotide, is called as RNA.

A "chimeric nucleic acid" means 2 mer or more nucleic acid, which is constructed from a DNA nucleotide and a RNA nucleotide.

A "template" means a single strand nucleic acid and it is constructed with DNA, RNA or a chimeric nucleic acid. A "primer" means a nucleic acid which has a complementary sequence to a part of the above template and hybridizes to a template. The primer is constructed with DNA, RNA or a chimeric nucleic acid and the 3'-end is used for DNA synthesis. Hybridization of "a template" and "a primer" can be performed by widely known methods in this field.

A "template", which is appropriate for the present invention, is RNA or a chimeric nucleic acid. A "primer", which is appropriate for the present invention, is DNA, RNA or a chimeric nucleic acid which has a sequence hybridizing to the template. Each can be represented by the following formulas.

Template: 5'-NRWXZ-3'

Primer: 3'-Y-5'

(Y hybridizes to X of a template,

N is 13-19 mer DNA, RNA or a chimeric nucleic acid,

R is RNA,

W is DNA or a chimeric nucleic acid,

X is 15 mer or more DNA, RNA or a chimeric nucleic acid,

Y is a same length DNA, RNA or a chimeric nucleic acid with X to which Y hybridizes.

In case that X to which Y hybridizes is DNA, Y is DNA. In case that X to which Y hybridizes is RNA, Y is RNA. In case that X to which Y hybridizes is a chimeric nucleic acid, Y is a chimeric nucleic acid (In the chimeric nucleic acid, in case that X to which Y hybridizes is DNA, Y is DNA. In case that X to which Y hybridizes is RNA, Y is RNA), Z is DNA, RNA or a chimeric nucleic acid.

(provided that, W and Z can be absent.))

As the other embodiment, they can be represented by the following formulas.

Template: 5'-NRWX-3'

Primer: 3'-YZ-5'

(Y hybridizes to X of a template,
N, R, W, X, Y and Z are the same meaning the above.)

"N" is a RNA, DNA and chimeric nucleic acid whose length is 1 nucleotide shorter than a length of distance between an RNase H active site and a polymerase active site of a reverse transcriptase. A 13-19 mer nucleic acid is preferable.

"R" is RNA comprising a bond which is cleaved in RNase H reaction after DNA synthesis proceeds to 5'-end of a template by the polymerase activity of a reverse transcriptase. It can be 1 mer or more RNA.

"W" can be DNA or a chimeric nucleic acid and the length is not restricted. Additionally, "W" can be absent.

"X" and "Y" can be RNA, DNA or a chimeric nucleic acid which have the complementary sequences and whose sugars of pair nucleotides in hybridizing are same. A reverse transcriptase has the polymerization-independent RNase H activity that the reverse transcriptase binds to double-stranded nucleic acid and cleaves the RNA of RNA: DNA hetero duplex. To prevent from hydrolysis of a template by this RNase H activity before the initiation of DNA synthesis reaction, "Y" is preferably a nucleic acid with a complementary sequence which is formed RNA: RNA or DNA: DNA homo duplex with a nucleic acid of "X" part to which Y hybridizes. In case that a length of a primer is shorter than 15 mer, efficiency of DNA synthesis is declined. To efficient screening of the present invention, "X" and "Y" are preferably nucleic acids that 15 or more and especially 18 or more nucleotides polymerized. From 15 mer to 30 mer length nucleotide is usually and widely used as a primer ("Y" part). Especially 18 mer-25 mer length is preferable.

"Z" is RNA, DNA or a chimeric nucleic acid and the length is not restricted. "Z" can be absent.

A reverse transcriptase binds by recognizing a phosphate group of a double strand which a template and a primer hybridized. An RNase H active site of a reverse transcriptase recognizes the RNA of RNA: DNA hetero duplex and cleaves it. The above recognition, binding and cleavage reactions are performed in sequence non-specific manner. Therefore, a template and a primer are not restricted with specific sequence and length if they are nucleic acids matched the above condition. In the other words, they are not restricted with specific sequence and length if they meet the requirement of N, R, W, X, Y, Z described in this description.

Length of a template or a primer can be suitably selected based on a kind of an enzyme. For example, 29-100 mer (preferably 29-50 mer) template and 15-50 mer (preferably 15-30 mer) primer can be used.

For example, when a template is RNA (For example, when 5'-NRWXZ-3' is that N is RNA, W is absent, X is RNA, Z is RNA or absent or when 5'-NRWX-3' is that N is RNA, W is absent, X is RNA.), the length is preferably 32 mer or more and especially preferably 37 mer or more.

When a template is 5'-NRWXZ-3' and RNA as the above, a primer (3'-Y-5') is RNA which hybridizes to RNA (X part) of a template and is preferably 15 mer or more and especially preferably 18 mer or more which is the same length with X.

When a template is 5'-NRWX-3' and RNA as the above, Y part of a primer (3'-YZ-5') is RNA which hybridizes to RNA (X part) of a template and is preferably 15 mer or more and especially preferably 18 mer or more which is the same length with X.

As the other embodiment, the followings are shown. For example, when a template is a chimeric nucleic acid with RNA at the side of 5'-end and DNA at the side of 3'-end (For example, when 5'-NRWXZ-3' is that N is RNA, W is DNA or absent, X is DNA, Z is DNA or absent, or when 5'-NRWX-3' is that N is RNA, W is absent, X is DNA), the template is a chimeric nucleic acid preferably with 17 mer or more RNA and 15 mer or more DNA and especially preferably with 19 mer or more RNA and 18 mer or more DNA.

When a template is 5'-NRWXZ-3' and a chimeric nucleic acid with RNA at the 5'-end and DNA at the 3'-end as the above, a primer (3'-Y-5') is DNA which hybridizes to DNA (X part) of a template and is preferably 15 mer or more and especially preferably 18 mer or more which is the same length with X.

When a template is 5'-NRWX-3' and a chimeric nucleic acid with RNA at the 5'-end and DNA at the 3'-end as the above, Y part of a primer (3'-YZ-5') is DNA which hybridizes to DNA (X part) of a template and is preferably 15 mer or more and especially preferably 18 mer or more which is the same length with X.

Especially, a template is a chimeric nucleic acid with RNA at the 5'-end and DNA at the 3'-end as the above, the combination of a template which is a chimeric nucleic acid with 19-25 mer RNA and 18-25 mer DNA at the 3'-end of RNA and 18-25 mer primer (DNA) is especially preferable.

Furthermore, a single stranded nucleic acid can be used as a substrate. For example, 3'-end of the above "a template" and 5'-end of the above "a primer" can be linked by a phosphodiester bond to be a single strand. The substrate like this can be represented by the following formula.

Substrate: 5'-NRWXZY-3'

(N, R, W, X, Z, Y are the same meanings the above.)

As a "metal ion", a divalent metal ion is preferable. For example, it is $Mg^{2+}$, $Mn^{2+}$, $Zn^{2+}$, $Ca^{2+}$, $Cu^{2+}$, $Co^{2+}$ or the like. Especially, $Mg^{2+}$ or $Mn^{2+}$ is preferable.

A "test substance" means a substance used for the screening, for example, a compound or a salt thereof. In this description, the above compound or the salt includes a low-molecular compound, a high-molecular compound, a polypeptide, a derivative thereof or the like. The test substance can be a natural substance or unnatural substance. The derivative of polypeptide is a modifying polypeptide obtained by adding a modifying group, a variant polypeptide obtained by reforming an amino acid residue or the like.

"dNTPs" means deoxynucleotide triphosphate and is composed of a substrate for DNA synthesis, deoxyadenyl triphosphate (dATP), deoxyguanosine triphosphate (dGTP), deoxycytidine triphosphate (dCTP) and/or deoxythymidine triphosphate (dTTP), which are substrates for DNA synthesis. dNTPs can be selected depending on a substrate for the present invention. For example, complementary dNTPs to a nucleic acid used as NRW part of a template (5'-NRWXZ-3' or 5'-NRWX-3') can be used. When NRW part of a template is DNA, RNA or a chimeric nucleic acid with any base sequence, a mixture of dATP, dGTP, dCTP and dTTP can be used as "dNTPs".

When a kind of nucleotide is used in a NRW part of a template, complementary dNTP can be used.

An "RNase H inhibitor of a reverse transcriptase" means a substance which inhibits RNase H enzyme reaction of a reverse transcriptase. As a parameter, a concentration of drug ($IC_{50}$ value) that causes 50% inhibition of an enzyme activity is usually used. As the inhibitor, $IC_{50}$ value of a substance is 100 µM or below, especially preferably 10 µM or below and more preferably 1 µM or below.

A "formation inhibitor of a complex of a reverse transcriptase, a substrate and a metal ion" is a compound which inhibits a complex formation with a reverse transcriptase, a substrate and a metal ion. In the present invention, it is used for preventing that a reverse transcriptase which does not bind to a substrate in process (b) binds to a substrate and expresses an enzyme activity in process (c), or that it forms a complex with a substrate and initiates RNase H reaction at a second time by turnover of a reverse transcriptase after the initiation of enzyme reaction by adding dNTPs in process (c).

As the formation inhibitor, a compound which inhibits a complex formation of a reverse transcriptase, a substrate and a metal ion can be used without restriction. For example, heparin, a double-stranded nucleic acid or the like can be used.

Now, as an inhibitor of a reverse transcriptase, nonnucleoside reverse transcriptase inhibitors such as Nevirapine are screened. These compounds are known to bind a nonnucleoside reverse transcriptase inhibitor binding site of reverse transcriptase of HIV. Furthermore, a virus with an Y188L mutant is acquired resistance against most nonnucleoside reverse transcriptase inhibitors known now.

In a screening method of the present invention, when HIV wild type reverse transcriptase is used, a test substance which inhibits the RNase H activity and the polymerase activity at a time by binding the RNaseH domain shows equivalence between the RNase H inhibitory activity and the polymerase inhibitory activity. Therefore, the measurement result is almost same with one of a test substance which is a nonnucleoside reverse transcriptase inhibitor.

Then, if an Y188L mutant enzyme whose tyrosine at residue 188 is mutated to leucine is used as a reverse transcriptase in the present invention, the test substance, which inhibits the polymerase activity of a reverse transcriptase and cross resistance to Nevirapine or the like, can be excluded. Therefore, an RNaseH inhibitor can be screened efficiently.

The present invention relates a screening method characterizing that the preincubation with a reverse transcriptase-substrate complex and a test substance under the presence of a metal ion can be performed by using the above an appropriate template and an appropriate primer. As the detecting method or the like, well-known methods can be used. The present invention is useful especially for a screening of a large number of compounds and especially for high throughput screening (HTS). The present invention can decrease noise (false-positive compounds) and select RNase H inhibitors efficiently.

As a screening method of the present invention, it is, concretely, a screening method comprising;
(a) a process to incubate a substrate which a primer hybridized to a template, a metal ion and a reverse transcriptase to form a complex,
(b) a process to add a test substance and incubate after the process (a),
(c) a process to add dNTPs after process (b) to initiate DNA synthesis,
(d) a process to measure the amount of nucleic acid cleaved from the template, and
(e) a process to compare the measured value with a measured value under the absence of a test substance.

The incubation in the above process (a) can be performed by mixing a substrate which a primer is hybridized to a template, a metal ion and a reverse transcriptase in a solution which does not prevent the natural functions of the reverse transcriptase, and maintaining it under an appropriate reaction condition, for example, at an appropriate reaction temperature for an appropriate reaction time.

The above "a solution which does not prevent the natural functions of the reverse transcriptase" is, for example, MOPS buffer, HEPES buffer, Tris buffer or the like.

The above "an appropriate reaction condition" is not especially restricted, for example, in a solution such as MOPS buffer, HEPES buffer, Tris buffer or the like, at pH6.0-10.0, preferably pH 7.0-8.0 and more preferably pH7.4 at 4° C.-50° C., preferably at 25° C.-37° C. and more preferably at 25° C. for 1 minute-1 hour, preferably for 5-20 minutes and more preferably for 10 minutes. In more detail, the appropriate reaction condition is, for example, in 50 mM MOPS (pH7.4), 10 mM $MgCl_2$, 1 mM DTT, 2 mM EDTA, 34 mM KCl, 0.48 nM substrate under the above condition.

The incubation of the above process (b) can be performed by mixing the above complex and a test substance in a solution which does not prevent the natural functions of the complex, and maintaining it under an appropriate reaction condition, for example, at an appropriate reaction temperature for an appropriate reaction time. The solution and the reaction condition can be same as the above incubation of process (a). An appropriate incubation time in process (b) is different depending on a test substance. Therefore, it is not especially restricted, but preferably for 5 minutes or more, more preferably for 10 minutes or more and much more preferably for 15 minutes or more. If the incubation of process (b) is not enough, an inhibitory activity of a test substance may not be detected.

DNA synthesis of the above process (c) can be performed by mixing the above complex and a test substance in a solution which does not prevent the natural functions of the a reverse transcriptase-substrate complex, and maintaining it under an appropriate reaction condition, for example, at an appropriate reaction temperature for an appropriate reaction time. The solution and the reaction condition can be same as the above incubation of process (a).

An assay for the amount of nucleic acids cleaved from a template in the above process (d) is not especially restricted. An assay which is generally known as an assay for the amount of nucleic acids in this field to measure an enzyme activity can be used. For example, a nucleic acid part cleaved from the above a template can be labeled in advance. It can be labeled with conventional fluorescent dye, a radioactive substance, digoxigenin or the like. As a labeled part, the 5'-end or 3'-end of a template is preferable. The detection of the amount of nucleic acids cleaved from a template can be performed by visualization with autoradiography or fluorescent substance, detection of a labeled template or the like in conventional modified polyacrylamide gel electrophoresis or the like. In detail, it is, for example, ELISA (Enzyme Linked Immuno Sorbent Assay), capillary electrophoresis, fluorescence energy transfer reaction, Homogeneous Time-Resolved Fluorescence (HTRF) or the like.

In process (e), the RNase H inhibitory activity is examined by comparing the result of the above process (d) and a measured value under the absence of a test substance. Under the absence of a test substance, a reverse transcriptase works by nature and a template at the side of 5'-end is cleaved. Therefore, a fragment of a nucleic acid which is shorter than a template used as a substrate is detected. When a measured value of short nucleic acid fragments in the above process (d) (the amount of nucleic acids) is equivalence or more than a measured value under the absence of a test substance, the test substance can not be an RNase H inhibitor. On the other hand, a measured value of a short nucleic acid fragment in the above process (d) (the amount of nucleic acids) is less than a measured value under the absence of a test substance or under a detection limit, the test substance can be an RNase H inhibitor.

However, a test substance may inhibit the polymerase activity like reverse transcriptase inhibitors known at present. In case that a test substance inhibits the polymerase activity, DNA synthesis does not initiate, the enzyme does not move and RNase H does not react. Therefore, a measured value of a short nucleic acid fragment in the above process (d) (the amount of nucleic acids) is less than a measured value under the absence of a test substance or under a detection limit. Therefore, for screening of an RNase H inhibitor, it's necessary to examine whether the test substance also inhibits the polymerase activity of a reverse transcriptase or not.

An examination method whether a test substance also inhibits the polymerase activity of a reverse transcriptase or not is not especially restricted. An assay which is well-known for the polymerase activity in this field can be used. For example, it is the RNA dependent DNA polymerase activity assay described in C. A. Shaw-Reid, et. al., The Journal of Biological Chemistry, Vol. 278, pp. 2777-2780 (2003) or the like.

Additionally, with this screening method, whether a test substance inhibits the polymerase activity of a reverse transcriptase or not can be examined. For example, it can be examined by measuring length of a primer after process (a)-(c). Under the absence of test substance, a reverse transcriptase works and a primer is elongated by the polymerase activity. Therefore, the nucleic acid which is longer than the primer used as a substrate is detected. The measured value of the longer primer than that in process (a) (the amount of nucleic acids) is equivalence or more than a measured value under the absence of a test substance, the test substance does not inhibit the polymerase activity. On the other hand, the measured value of the longer primer than that in process (a) (the amount of nucleic acids) is less than a measured value under the absence of a test substance or under a detection limit, the test substance inhibits the polymerase activity.

Assay for the amount of a primer elongated by DNA synthesis is not especially restricted. An assay which is generally known as an assay for measuring the amount of nucleic acids can be used. For example, the above primer can be labeled in advance. It can be labeled with conventional fluorescent dye, a radioactive substance, digoxigenin or the like. As a labeled part, the 5'-end of a primer is preferable. The detection of the primer can be performed by visualization with autoradiography or fluorescent substance, detection of a labeled primer or the like in conventional modified polyacrylamide gel electrophoresis or the like. In detail, it is, for example, ELISA, capillary electrophoresis, fluorescence energy transfer reaction, Homogeneous Time-Resolved Fluorescence (HTRF) or the like.

However, among test substances which are judged as a polymerase inhibitor by the above method, there may be substances which inhibit the RNase H activity and the polymerase activity at a time by binding an RNase H domain. In the case of a test substance like this, the inhibition to elongate a primer and the inhibition to cleavage a template show the equivalence. As a result, length of a primer does not change comparing to that in process (a). Therefore, the measurement result is almost same with the result of a reverse transcriptase inhibitor by a well-known mechanism of action at present (a compound which inhibits the polymerase activity by binding the polymerase active site or the nonnucleoside binding site).

By the above measurement result of the inhibition of the RNase H activity and the polymerase activity, a test substance can be judged like Table 1. The result is compared to the measured amount of nucleic acids under the presence of a test substance.

TABLE 1

| Test substance | The amount of nucleic acids of short nucleic acid fragments in Process (d) (comparing to control) | The amount of nucleic acids of an elongated primer (comparing to control) |
| --- | --- | --- |
| A substance which does not inhibit both the RNase H activity and the polymerase activity | Equivalence | Equivalence |
| A substance which specifically inhibits the RNase H activity without inhibiting the polymerase activity | Decrease | Equivalence |
| A substance which inhibits the polymerase activity through a known mechanism of action | Decrease | Decrease |
| A substance which inhibits the RNase H activity and the polymerase activity at a time by binding an RNase H domain | Decrease | Decrease |

Like Table 1, by the above method, a substance which inhibits the RNase H activity and the polymerase activity at a time by binding an RNase H domain and a reverse transcriptase inhibitor through a well-known mechanism of action at present (a compound which inhibits the polymerase activity by binding the polymerase active site or the non-nucleoside inhibitor binding site) can not be distinguished. As to an RNase H inhibitor through this mechanism, the experiment is performed with an enzyme introducing a mutation at an RNase H active site or the like to identify a mechanism of action. In the other word, as to a test substance which inhibits the RNase H activity and the polymerase activity at a time, by an assay for a well-known the RNase H activity and a screening method of the present invention with a well-known reverse transcriptase with a mutation near a polymerase active site, for example, an Y188L mutant enzyme or the like, or a well-known reverse transcriptase with a mutation near an RNase H active site, for example, an Y501W mutant enzyme or the like, whether the test substance regulates the function by binding the polymerase active site or the RNase H active site or not can be examined.

A metal ion is essential factor for the activities of a reverse transcriptase and known to bind at an RNase H active site and a polymerase active site. By an assay for a well-known RNase H activity and a screening method of the present invention with a well-known reverse transcriptase with a mutation at a polymerase active site in this field, for example, a D185N mutant enzyme or the like, or a reverse transcriptase mutation at an RNase H active site, for example, a D443N mutant enzyme or the like, whether the test substance control the function by directly binding the polymerase active site or the RNase H active site through a metal ion or not can be examined.

A compound or a salt thereof obtained by the screening method of the present invention can show the therapeutic or the preventive activity against a disease caused by a pathogen (for example, HIV or the like) with a reverse transcriptase having the RNase H activity. Therefore, a compound or a salt thereof obtained by the above screening method provides a pharmaceutical composition for treatment or prevention against RNase H related diseases, for example, AIDS or the like.

A pharmaceutical composition containing a compound or a salt thereof obtained by the screening method of the present invention as an active ingredient has a beneficial effect that it can be act through the inhibition of the RNase H against the above disease related to the RNase H function or a disease related to the function. Additionally, the pharmaceutical composition has a beneficial effect that it can be act through the inhibition of the RNase H function against AIDS related to the above function. Therefore, the pharmaceutical composition has a beneficial effect that it can improve viral diseases through the different mechanism of action from that of existing anti-virus drug by inhibiting the activity of polymerase, integrase and protease.

The content of the above a compound or a salt thereof in the above pharmaceutical composition can be suitably controlled depending on a disease which is a therapeutic purpose, age, body weight of the patient or the like. It may be effective dose for therapy. In case of a low-molecular compound or a high-molecular compound, it is, for example, 0.0001-1000 mg and preferably 0.001-100 mg. In case of a polypeptide or the derivative, it is, for example, 0.0001-1000 mg and preferably 0.001-100 mg.

The above pharmaceutical composition can additionally comprise different auxiliaries which can maintain stably the above compound or a salt thereof To be more precise, it is a pharmaceutical acceptable auxiliary with the character that it inhibits the degradation of active ingredient before reaching a part which is an object to send an active ingredient, for example, excipient, binding agent, stabilizing agent, buffer agent, solubilizing agent, isotonic agent or the like.

The administration of the above pharmaceutical composition is suitably selected depending on a kind of an active ingredient; an individual, an organ, a local part or an organization which is an object of the administration; the age or the body weight of an individual who is an object of the administration or the like. The above administration is, for example, hypodermic injection, muscle injection, intravenous injection, local administration or the like.

Furthermore, the dosage of the above pharmaceutical composition is also suitably selected depending on a kind of an active ingredient; an individual, an organ, a local part or an organization which is an object of the administration; the age or the body weight of an individual who is an object of the administration or the like. The dosage is not especially restricted. It is at few times per 1 day, for example, at 1-3 times or the like. The dosage of the active ingredient at one time is, for example, 0.0001-1000 mg/kg weight and preferably 0.001-100 mg/kg weight when an active ingredient is a low-molecular compound or a high-molecular compound and it is, for example, 0.0001-1000 mg/kg weight, preferably, 0.001-100 mg/kg weight when an active ingredient is a polypeptide or the derivative.

EXAMPLE 1

Preparation of a Substrate

Figure 1:
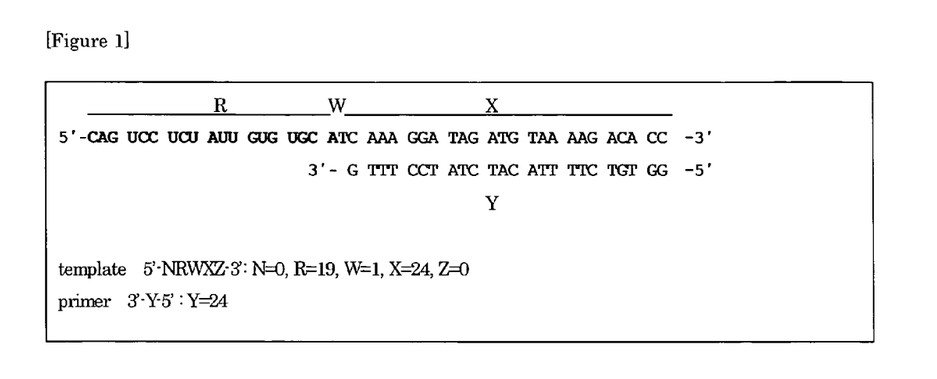
[FIG. 1] The structure of the chimeric substrate.

A substrate which DNA primer synthesized by QIAGEN was hybridized to RNA-DNA chimeric nucleic acid synthesized by Proligo (FIG. 1) was used as a substrate. The template labeled at 5'-end of the template to examine the RNase H activity inhibitory activity or the primer labeled at 5'-end of the primer to examine the polymerase activity by using T4 polynucleotide kinase and [$\gamma$-$^{32}$P] ATP was used. After purifying with modified polyacrylamide gel electrophoresis, the labeled nucleic acid was mixed with equimolar unlabeled complementary strand in KTE buffer solution (Composition: 80 mM KCl, 1 mM EDTA, 10 mM Tris-HCl (pH 8.0)). The mixture was heated at 85° C. for 15 minutes and then cooled slowly to hybridize complementary strands.

EXAMPLE 2

Enzyme Reaction 10.25 μl of the enzyme reaction solution (Composition: 50 mM MOPS (pH 7.4), 10 mM MgCl$_2$, 1 mM DTT, 2 mM EDTA, 34 mM KCl, 0.48 nM substrate) was divided to polypropylene tubes. Next, an enzyme solution (0.1 pmol reverse transcriptase) 1 μl containing reverse transcriptase of HIV was added thereto and mixed well. After incubation at room temperature for 10 minutes, a test compound, positive control (PC) or negative control (NC) in DMSO solution 1.25 μl was added thereto and mixed well. After incubation at a room temperature for 15 minutes, reaction initiating solution (Composition: 1 mg/mL heparin, 0.1 mM dNTPs) 1 μl was added thereto and the mixture was incubated at a room temperature for 10 minutes. Then a reaction stop solution (Composition: 45% formamide, 5 mM EDTA, 0.05% bromo phenol blue, 0.05% xylene cyanol) 12. 5 μl was added thereto. As to NC, before adding a reaction initiating solution, a reaction stop solution 12. 5 μl was added to stop the reaction in advance. All of the above declared concentrations were final concentrations.

EXAMPLE 3

Assay of an Inhibiting Rate

The reaction solution was heated at 85° C. for 5 minutes and cooled on ice for 2 minutes and electrophoresis with modified polyacrylamide gel (Gel composition: 8M urea, 20% acrylamide) was performed to isolate reaction products. By BAStation ver. 3.0 (Fujifilm), the band strength of reaction products was determined and RNase H reaction inhibiting rate or polymerase reaction inhibiting rate was calculated by the following formula. An RNase H inhibitor (Compound 1; 4-[5-(benzoylamino)thien-2-yl]-2,4-dioxobutanoic acid) as a test compound, Suramin sodium which non-specifically binds to a reverse transcriptase and Nevirapine which is a nonnucleoside reverse transcriptase inhibitor as a control compound were used.

Figure 2:
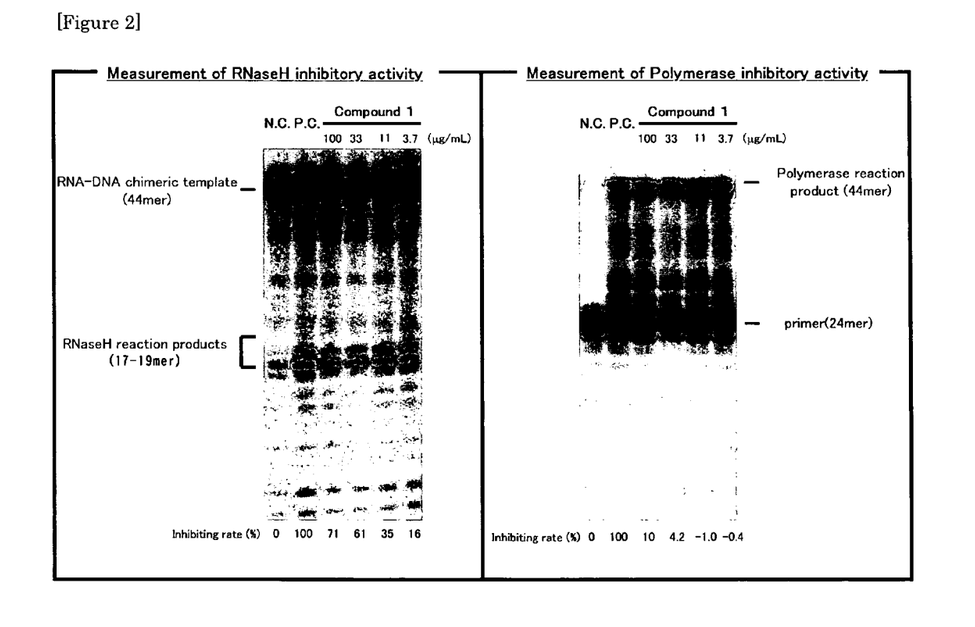
[FIG. 2] An RNase H inhibiting rate or a polymerase inhibiting rate of Compound 1 when that a HIV Y188L mutant enzyme was used.
Figure 3:
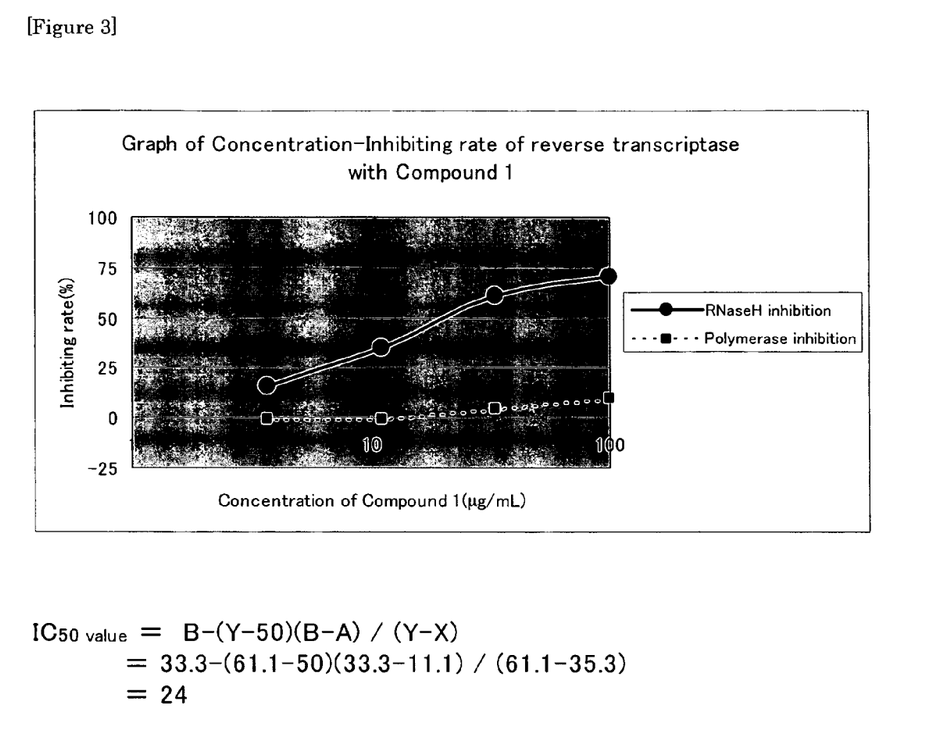
[FIG. 3] Condensation-inhibiting rate curve of Compound 1 when that a HIV Y188L mutant enzyme was used.

FIG. 2 shows an autoradiography figure of Compound 1 and inhibiting rate calculated by the following Formula 1. FIG. 3 shows concentration-inhibitory curve of Compound 1. Table 2 shows IC$_{50}$ value when a wild type reverse transcriptase of HIV was used. IC$_{50}$ value was calculated by the following Formula 2. The unit is μg/ml. Table 3 shows IC$_{50}$ value when an Y188L mutant enzyme of HIV was used. IC$_{50}$ value was calculated by the following Formula 2. The unit is μg/ml. All of the above declared concentrations were final concentrations.

Inhibiting rate(%)=100[1-{(C density−NC density)/ (PC density−NC density)}]    [Formula 1]

C density: Band strength of enzyme reaction products when a compound is added

NC density: Band strength of enzyme reaction products of NC

PC density: Band strength of enzyme reaction products of PC

IC50 value=B−(Y−50)(B−A)/(Y−X)    [Formula 2]

X; An inhibiting rate when the compound concentration is A

Y; An inhibiting rate when the compound concentration is B

A, B; The compound concentration at two point sandwiched Inhibiting rate 50%.

TABLE 2

| No. | Without preincubation(a) | | With preincubation | | | |
|---|---|---|---|---|---|---|
| | | | Without metal cofactors(b) | | With metal cofactors | |
| | RNaseH | Polymerase | RNaseH | Polymerase | RNaseH | Polymerase |
| Compound 1 | >100 | >100 | >100 | >100 | 30 | >100 |
| suramin | >100 | >100 | ≈POL | 21 | ≈POL | 3.2 |
| nevirapine | ≈POL | 10 | ≈POL | 0.18 | ≈POL | 0.34 |

(a) Without preincubation; Adding DMSO solution of a test compound and a reaction initiating solution at a time to a reverse transcriptase-substrate complex formed under the presence of metal cofactors.
(b) With preincubation and without metal cofactors; Forming a reverse transcriptase-substrate complex under the absence of metal cofactors, adding DMSO solution of a test compound, preincubating and then adding metal cofactors and a reaction initiatng solution at a time thereto.

TABLE 3

| No. | Without preincubation | | With preincubation | | | |
|---|---|---|---|---|---|---|
| | | | Without metal cofactors | | With metal cofactors | |
| | RNaseH | Polymerase | RNaseH | Polymerase | RNaseH | Polymerase |
| Compound 1 | >100 | >100 | >100 | >100 | 24 | >100 |
| suramin | >100 | >100 | ≈POL | 13 | ≈POL | 3.2 |
| nevirapine | >100 | >100 | >100 | >100 | >100 | >100 |

The value is IC50 (μg/mL)

From these results, compound 1 is an RNase H inhibitor which specifically inhibits the RNase H activity without inhibiting a polymerase reaction. However, to detect the inhibitory activity sensitively, the preincubation of the compound and a reverse transcriptase-substrate complex formed under the presence of metal ion is necessary. When an Y188L mutant enzyme to which a nonnucleoside reverse transcriptase inhibitor has resistance was used instead of a wild-type reverse transcriptase, the polymerase inhibitory activity of Nevirapine distinguished but the inhibitory activity of Suramin sodium is almost equivalence. Therefore, by using an Y188L mutant enzyme instead of a wild-type reverse transcriptase, the possibility that a test substance which has cross resistance with Nevirapine or the like inhibits the enzyme activity can be excluded and the objective RNase H inhibitor can be efficiently screened. Suramin sodium inhibits the polymerase activity and the RNase H activity at a time but there is the low possibility that it is a nonnucleoside reverse transcriptase inhibitor. It is reported the inhibitory activity in various enzyme assays and it is said a non-specific protein binding substance.

EXAMPLE 4

Assay of an Inhibiting Rate with Fluorescence Energy Transfer Reaction

3'-end of a template is labeled with digoxigenin and immobilized on an assay plate. 5'-end of a template is labeled with fluorescent substance such as 6-FAM or the like. Deoxynucleotide triphosphate labeled with TAMRA or the like which is a quencher of fluorescent substances is added to dNTPs in advance and a base sequence of a template or a primer is constructed so that deoxynucleotide-quencher incorporated by the polymerase reaction is near the fluorescent substance when the polymerase reaction is finished and the fluorescence from the fluorescent substance can be quenched. After finishing the reaction, the polymerase inhibitory activity can be evaluated by measuring the degree of quenching of 6-FAM. Next, after washing under the condition that template fragments cleaved by the RNase H activity are detached from the assay plate, fluorescence by 6-FAM remained on the plate is measured to evaluate the RNase H inhibitory activity. As a result, a candidate compound of an RNase H inhibitor of a reverse transcriptase is screened.

EXAMPLE 5

Assay of an Inhibiting Rate with Capillary Electrophoresis

In stead that the substrate is labeled with RI, 2 kinds of fluorescent substance are used. For example, the substrate which a primer labeled at the 5'-end with PET™ is hybridized to a chimeric template labeled at the 5'-end with 6-FAM is used. After the reaction, 2.5 μL of 90 mM EDTA solution is added thereto to stop the reaction. The solution 10 μL that GeneScan 120 LIZ Size Standard is diluted 60 times with Hi Di Formamide to the reaction solution 3 μL is added thereto, heated at 85° C. for 5 minutes and cooled on ice for 2 minutes. Then capillary electrophoresis was performed by ABI PRISM 3100. The migration result is analyzed by GeneMapper3.5. The RNase H activity is obtained by the determination of the peak amount of cleaved 6-FAM labeled nucleic acid and the polymerase activity is obtained by the determination of the peak amount of PET™ labeled nucleic acid elongated to 44 mer. As the result, a candidate compound of an RNase H inhibitor is screened.

INDUSTRIAL APPLICABILITY

By using a screening method of the present invention, a compound which inhibits the polymerization-dependent RNase H activity can be efficiently screened. An RNase H inhibitor screened is an anti-virus drug through a new mechanism of action and an anti-virus drug which effects on resistant viruses against polymerase inhibitors, integrase inhibitors and protease inhibitors can be developed.

The invention claimed is:

1. A screening method for an RNase H inhibitor of a reverse transcriptase, comprising;
   (a) incubating a substrate which is a primer hybridized to a template, a metal ion and a reverse transcriptase to form a complex,
   (b) adding a test substance after the process (a) and further incubating, and
   (c) adding dNTPs after process (b) to initiate DNA synthesis,
   (d) measuring the amount of nucleic acid cleaved from the template after the process (c), and
   (e) comparing the value from step (d) to a control lacking the test substance provided that:
   the template is 5'-NRWXZ-3' and the primer is 3'-Y-5', the template is 5'-NRWX-3' and the primer is 3'-YZ-5', or the 3' end of the template 5'-NRWXZ-3' is linked to the 5' end of primer 3'-Y-5' to be a single strand to form -substrate 5'-NRWXZY-3',
   wherein,
   N is present or absent, and if present N is a nucleic acid
   R is RNA, and the total length of N plus R is 14 mer or more,
   W is present or absent and if present W is DNA or a chimeric nucleic acid,
   X is a nucleic acid 15 or more nucleotides long,
   Y is a nucleic acid with the same length as X to which Y hybridizes;
   wherein if X is DNA, then Y is DNA; if X is RNA, then Y is RNA; and if X is a chimeric nucleic acid, then Y is a chimeric nucleic acid having complementary sequences and whose sugars of pair nucleotides are the same;
   Z is present or absents and if present, is a nucleic acid.

2. The screening method of claim 1, wherein N is RNA, W is absent, X is RNA, and Y is RNA.

3. The screening method of claim 1, wherein N is RNA, W is absent, X is DNA, and Y is DNA.

4. The screening method of any one of claims 1-3, wherein X is 18 mer or more DNA, RNA or a chimeric nucleic acid.

5. The screening method of any one of claims 1-3, wherein the metal ion is $Mg^{2+}$ or $Mn^{2+}$.

6. The screening method of claim 1, wherein a formation inhibitor to a complex of a reverse transcriptase, a substrate and a metal ion is added with dNTPs in process (c).

7. The screening method of claim 6, wherein the formation inhibitor is heparin.

8. The screening method of claim 1 wherein the template is a template whose 5'-end or 3'-end is labeled.

9. The screening method of claim 1, wherein the reverse transcriptase is a reverse transcriptase of a virus.

10. The screening method of claim 9, wherein the virus is HIV.

11. The screening method of claim 9, wherein the reverse transcriptase is Y188L mutant enzyme.

12. The screening method of claim 9, wherein the reverse transcriptase is a mutant RNase H enzyme.

\* \* \* \* \*